US011797354B2

(12) United States Patent
O'Donoghue et al.

(10) Patent No.: US 11,797,354 B2
(45) Date of Patent: *Oct. 24, 2023

(54) ENSEMBLE MACHINE LEARNING FRAMEWORK FOR PREDICTIVE OPERATIONAL LOAD BALANCING

(71) Applicant: Optum Services (Ireland) Limited, Dublin (IE)

(72) Inventors: Kieran O'Donoghue, Dublin (IE); Michael J. McCarthy, Castleknock (IE); Neill Michael Byrne, Dublin (IE); David Lewis Frankenfield, Highlands Ranch, CO (US)

(73) Assignee: Optum Services (Ireland) Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/048,556

(22) Filed: Oct. 21, 2022

(65) Prior Publication Data

US 2023/0066201 A1    Mar. 2, 2023

Related U.S. Application Data

(63) Continuation of application No. 15/931,168, filed on May 13, 2020, now Pat. No. 11,526,383.

(51) Int. Cl.
*G06F 9/50* (2006.01)
*G06N 20/00* (2019.01)

(52) U.S. Cl.
CPC .......... *G06F 9/5083* (2013.01); *G06N 20/00* (2019.01)

(58) Field of Classification Search
None
See application file for complete search history.

(56) References Cited

U.S. PATENT DOCUMENTS

| 8,515,777 B1 | 8/2013 | Rajasenan |
| 10,554,738 B1 | 2/2020 | Ren |
| 2020/0105400 A1 | 4/2020 | Alvelda et al. |

(Continued)

FOREIGN PATENT DOCUMENTS

WO    2018/206374 A1    11/2018

OTHER PUBLICATIONS

"Actuarial Standard of Practice No. 45—The Use of Health Status Based Risk Adjustment Methodologies," Actuarial Standards Board, Jan. 2012, (19 pages).

(Continued)

*Primary Examiner* — Michael Alsip
(74) *Attorney, Agent, or Firm* — ALSTON & BIRD LLP

(57) ABSTRACT

There is a need for more effective and efficient constrained-optimization-based operational load balancing. In one example, a method comprises determining constraint-satisfying operator-unit mapping arrangements that satisfy an operator unity constraint and an operator capacity constraint; for each constraint-satisfying operator-unit mapping arrangement, determining an arrangement utility measure; processing each arrangement utility measure using an optimization-based ensemble machine learning model that is configured to determine an optimal operator-unit mapping arrangement of the plurality of constraint-satisfying operator-unit mapping arrangements; and initiating the performance of one or more operational load balancing operations based on the optimal operator-unit mapping arrangement.

20 Claims, 13 Drawing Sheets

(56) References Cited

U.S. PATENT DOCUMENTS

2021/0357268 A1 11/2021 O'Donoghue et al.

OTHER PUBLICATIONS

Chen, Jonathan H. et al. "Machine Learning and Prediction in Medicine—Beyond the Peak of Inflated Expectations," New England Journal of Medicine, Jun. 29, 2017, vol. 376, No. 26, pp. 2507-2509. DOI: 10.1056/NEJMp1702071.

Hileman, Geoffrey R. et al. "Risk Scoring in Health Insurance: A Primer," Society of Actuaries, (2016), pp. 1-27. [Retrieved from the Internet Aug. 7, 2020] <https://www.soa.org/globalassets/assets/Files/Research/research-2016-risk-scoring-health-insurance.pdf>.

500

| Member | Medical Condition | Probability |
|---|---|---|
| John Doe | Diabetes | 0.79 |
| John Doe | Congestive Heart Failure | 0.99 |
| Jane Doe | Congestive Heart Failure | 0.40 |

| Medical Chart | Medical Condition | Probability |
|---|---|---|
| 551 Chart No. 11111 | Chronic Obstructive Pulmonary Disease | 0.46 |
| 552 Chart No. 22222 | Chronic Kidney Disease 562 | 0.88 |
| Chart No. 22222 | Chronic Obstructive Pulmonary Disease 561 | 0.39 |

FIG. 5B

| Operator | Medical Condition | Quality/Yield/Expertise |
|---|---|---|
| Anne James | Diabetes 611 | 0.90 (High bucket) |
| Fred Grimes | Congestive Heart Failure 612 | 0.20 (Low Bucket) |

| Operator | Cost per unit time | Scheduled maximum time units in Time Window |
|---|---|---|
| Anne James | $25 | 39 |
| Fred Grimes | $23 | 47 |

700

601 (Anne James row)
602 (Fred Grimes row)

| Medical Condition or Disease family | Risk Adjustment Savings |
|---|---|
| 801 Diabetes with Complications | $2,500 |
| 802 Chronic Kidney Disease | $1,500 |

FIG. 8

| Operator | | Work Unit | |
|---|---|---|---|
| 601 | Anne James | Chart No. 139914 | 911 |
| 601 | Anne James | Chart No. 237486 | 912 |
| 602 | Fred Grimes | Chart No. 98798 | 913 |
| 602 | Fred Grimes | Chart No. 8765 | 914 |

FIG. 9

ENSEMBLE MACHINE LEARNING FRAMEWORK FOR PREDICTIVE OPERATIONAL LOAD BALANCING

CROSS REFERENCE TO RELATED APPLICATIONS

This application is a continuation of U.S. application Ser. No. 15/931,168 filed May 13, 2020, the contents of which are incorporated herein by reference in its entirety.

BACKGROUND

Various embodiments of the present invention address technical challenges related to performing predictive operational load balancing across a variety of operational systems. In doing so, various embodiments of the present invention address many shortcomings of existing operational load balancing solutions and disclose various techniques for efficiently and reliably performing predictive operational load balancing operations.

BRIEF SUMMARY

In general, embodiments of the present invention provide methods, apparatus, systems, computing devices, computing entities, and/or the like for initiating the performance of one or more load balancing operations.

In accordance with one aspect, a method is provided. In one embodiment, the method comprises determining a plurality of constraint-satisfying operator-unit mapping arrangements that satisfy an operator unity constraint and an operator capacity constraint, wherein (i) in accordance with the operator unity constraint, each constraint-satisfying operator-unit mapping arrangement maps each work unit profile of the plurality of work unit profiles to an operator profile of the plurality of operator profiles, and (ii) in accordance with the operator capacity constraint, each total operator utilization measure for an operator profile of the plurality of operator profiles under a constraint-satisfying operator-unit mapping arrangement of the plurality of constraint-satisfying operator-unit mapping arrangements satisfies an estimated capacity of the operator profile; for each constraint-satisfying operator-unit mapping arrangement, determining an arrangement utility measure that describes an estimated utility of utilizing mappings between the plurality of operator profiles and the plurality of work unit profiles using an optimization-based ensemble machine learning model; determining an optimal operator-unit mapping arrangement based at least in part on each arrangement utility measure for a constraint-satisfying operator-unit mapping arrangement of the plurality of constraint-satisfying operator-unit mapping arrangements; and initiating the performance of one or more operational load balancing operations based at least in part on the optimal operator-unit mapping arrangement.

In accordance with another aspect, a computer program product is provided. The computer program product may comprise at least one computer-readable storage medium having computer-readable program code portions stored therein, the computer-readable program code portions comprising executable portions configured to determine a plurality of constraint-satisfying operator-unit mapping arrangements that satisfy an operator unity constraint and an operator capacity constraint, wherein (i) in accordance with the operator unity constraint, each constraint-satisfying operator-unit mapping arrangement maps each work unit profile of the plurality of work unit profiles to an operator profile of the plurality of operator profiles, and (ii) in accordance with the operator capacity constraint, each total operator utilization measure for an operator profile of the plurality of operator profiles under a constraint-satisfying operator-unit mapping arrangement of the plurality of constraint-satisfying operator-unit mapping arrangements satisfies an estimated capacity of the operator profile; for each constraint-satisfying operator-unit mapping arrangement, determine an arrangement utility measure that describes an estimated utility of utilizing mappings between the plurality of operator profiles and the plurality of work unit profiles using an optimization-based ensemble machine learning model; determine an optimal operator-unit mapping arrangement based at least in part on each arrangement utility measure for a constraint-satisfying operator-unit mapping arrangement of the plurality of constraint-satisfying operator-unit mapping arrangements; and initiate the performance of one or more operational load balancing operations based at least in part on the optimal operator-unit mapping arrangement.

In accordance with yet another aspect, an apparatus comprising at least one processor and at least one memory including computer program code is provided. In one embodiment, the at least one memory and the computer program code may be configured to, with the processor, cause the apparatus to determine a plurality of constraint-satisfying operator-unit mapping arrangements that satisfy an operator unity constraint and an operator capacity constraint, wherein (i) in accordance with the operator unity constraint, each constraint-satisfying operator-unit mapping arrangement maps each work unit profile of the plurality of work unit profiles to an operator profile of the plurality of operator profiles, and (ii) in accordance with the operator capacity constraint, each total operator utilization measure for an operator profile of the plurality of operator profiles under a constraint-satisfying operator-unit mapping arrangement of the plurality of constraint-satisfying operator-unit mapping arrangements satisfies an estimated capacity of the operator profile; for each constraint-satisfying operator-unit mapping arrangement, determine an arrangement utility measure that describes an estimated utility of utilizing mappings between the plurality of operator profiles and the plurality of work unit profiles using an optimization-based ensemble machine learning model; determine an optimal operator-unit mapping arrangement based at least in part on each arrangement utility measure for a constraint-satisfying operator-unit mapping arrangement of the plurality of constraint-satisfying operator-unit mapping arrangements; and initiate the performance of one or more operational load balancing operations based at least in part on the optimal operator-unit mapping arrangement.

BRIEF DESCRIPTION OF THE DRAWINGS

Figure 1:
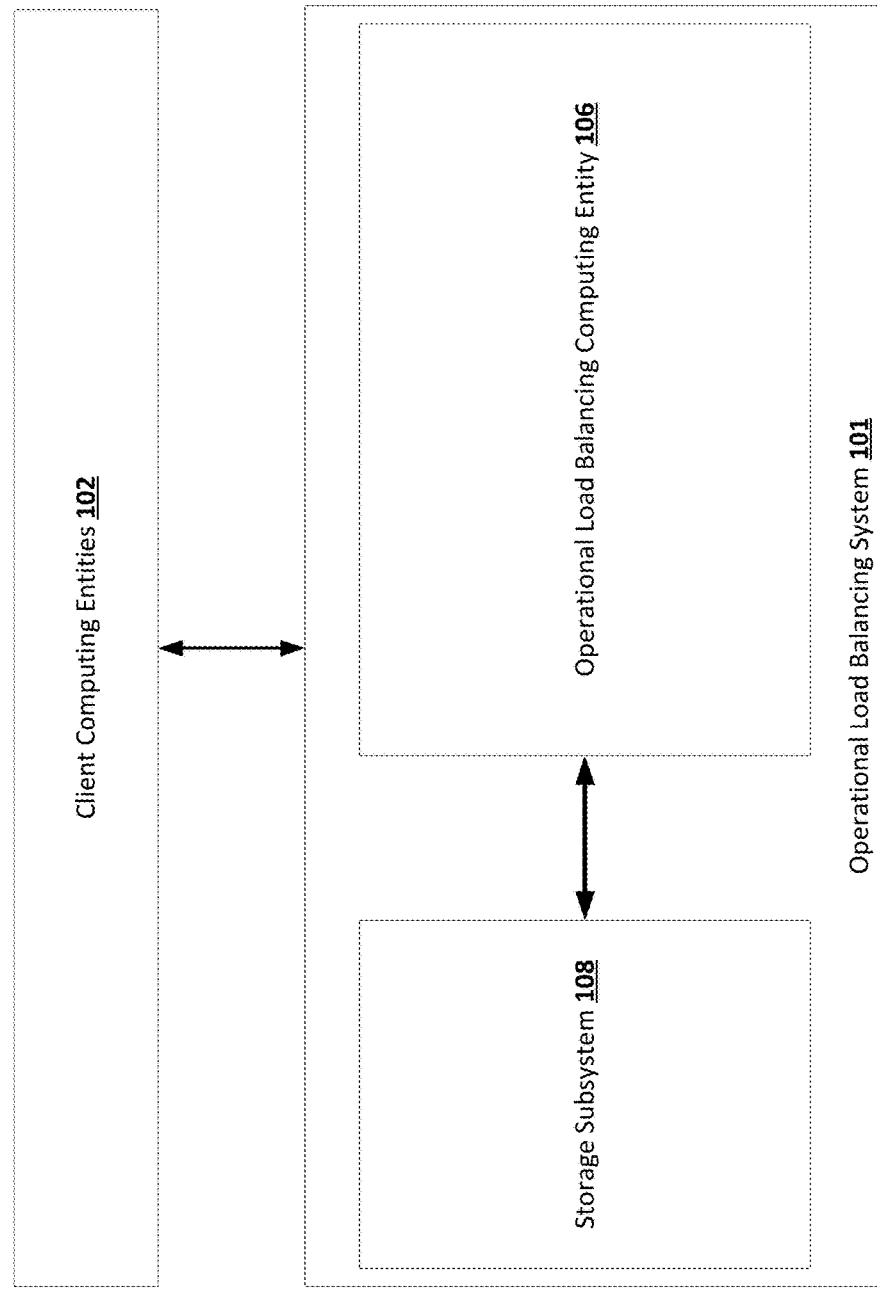

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
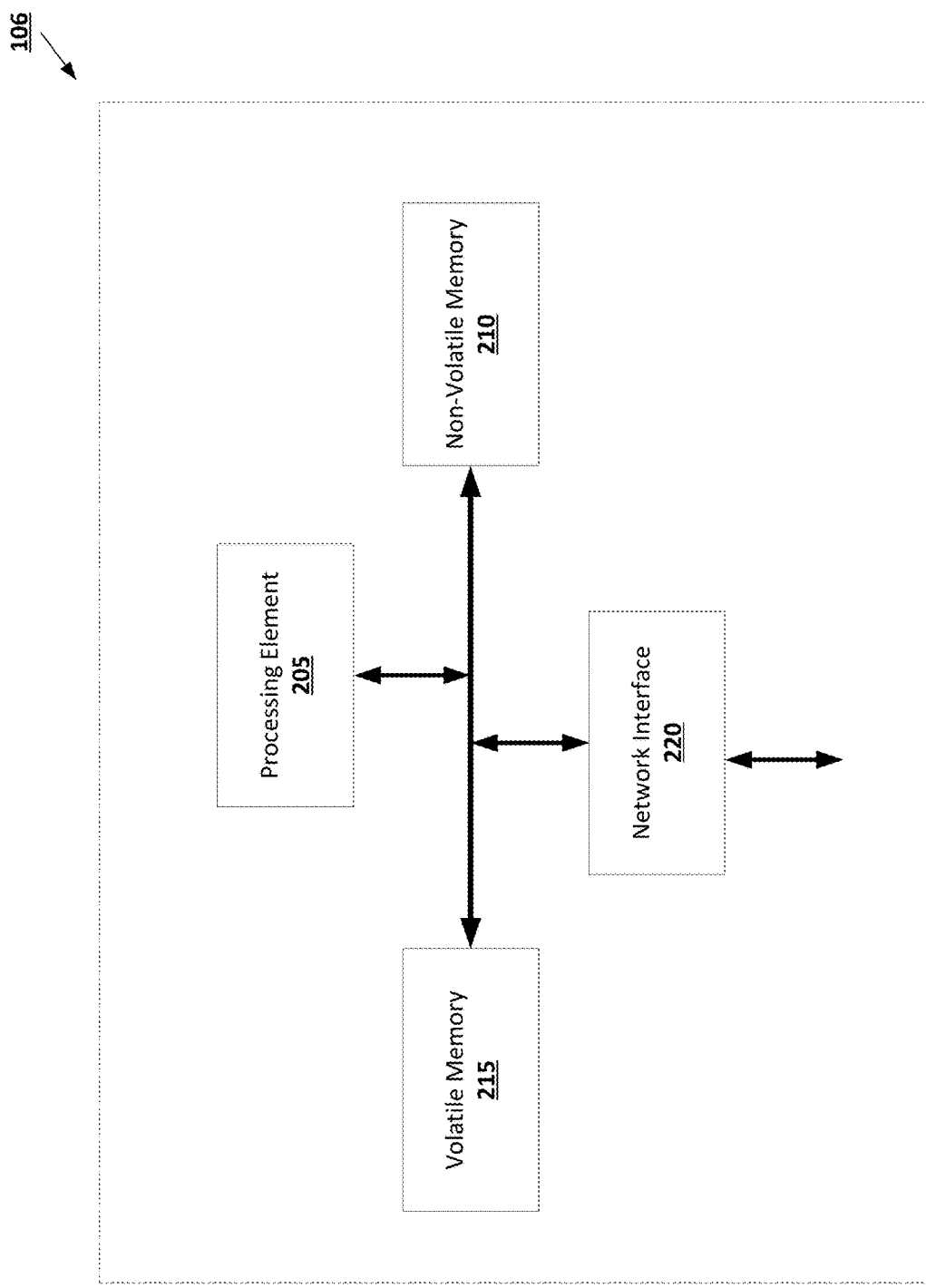

FIG. 2 provides an example operational load balancing computing entity in accordance with some embodiments discussed herein.

Figure 3:
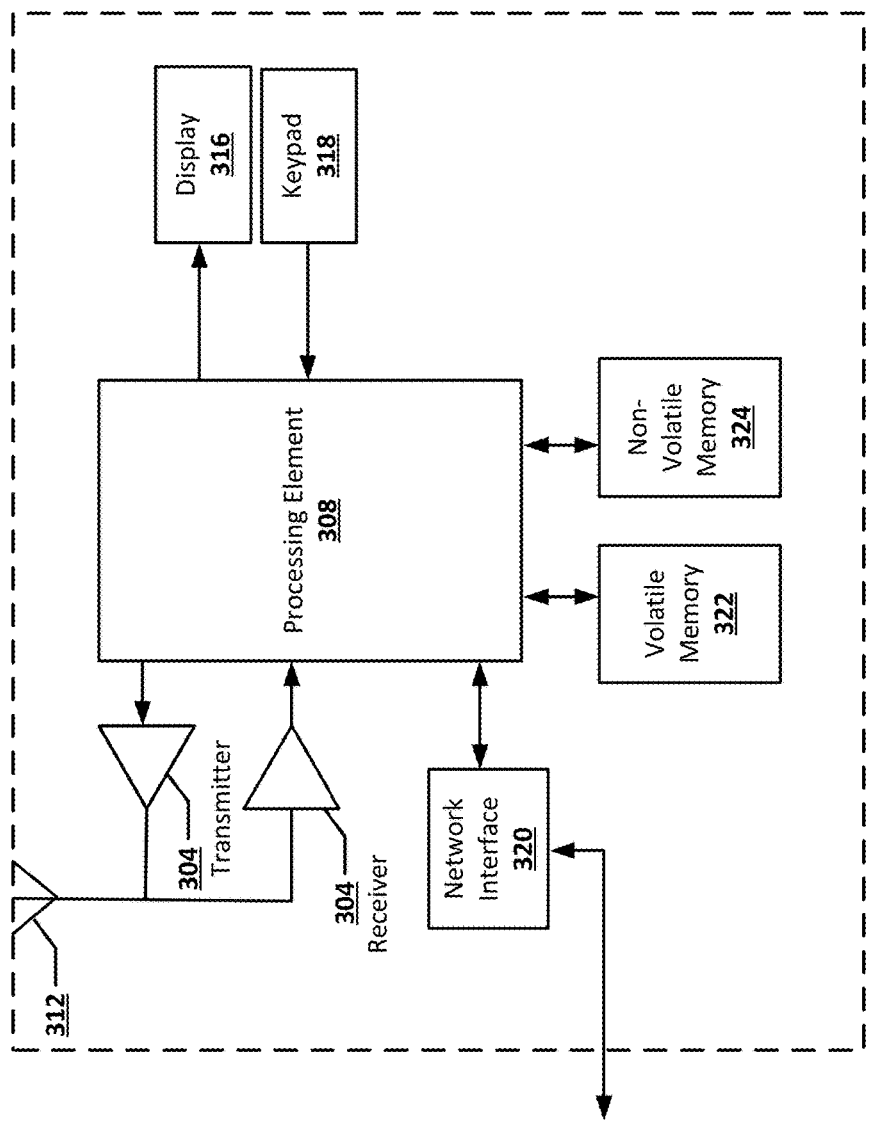

FIG. 3 provides an example client computing entity in accordance with some embodiments discussed herein.

Figure 4:
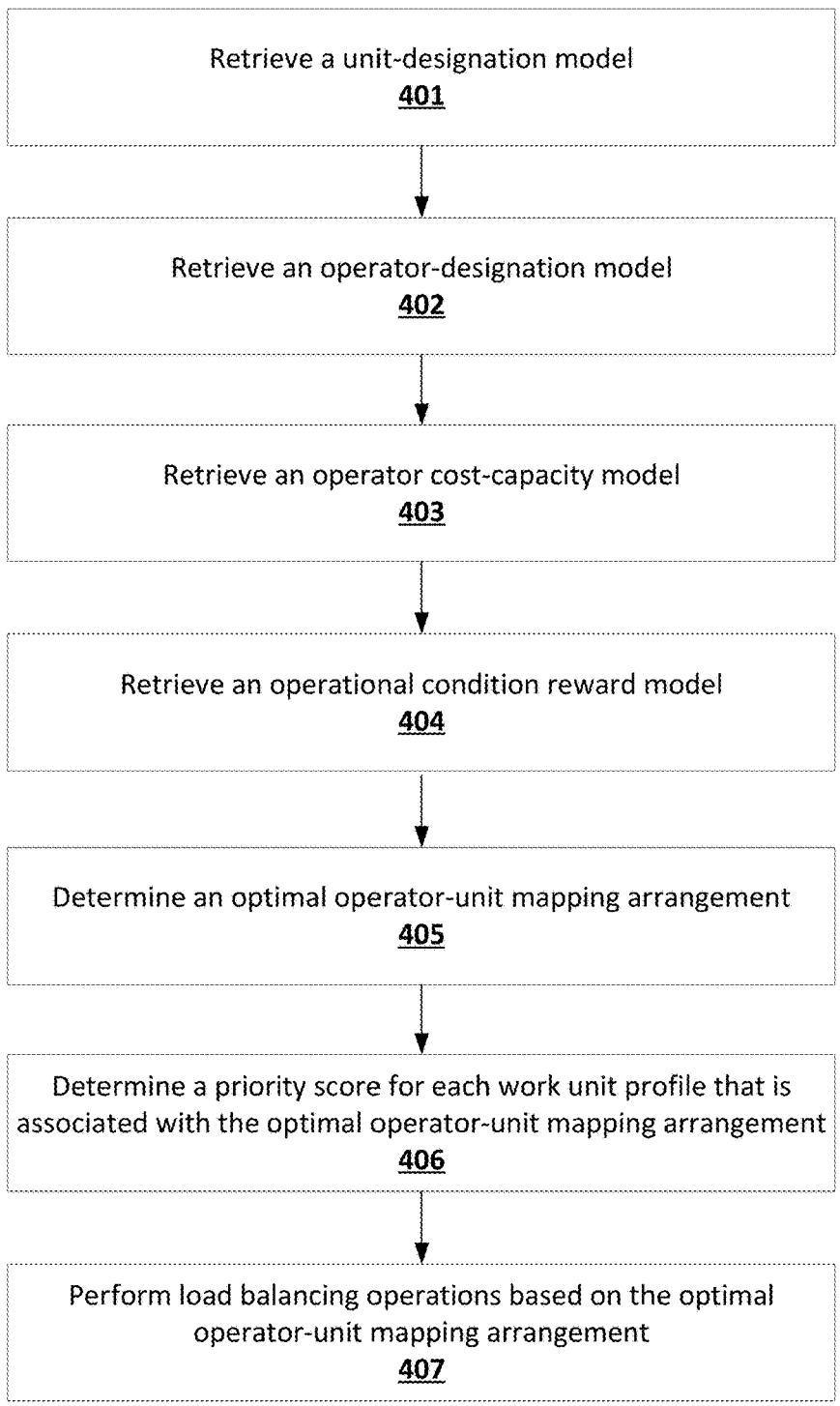

FIG. 4 is a flowchart diagram of an example process for performing constrained-optimization-based operational load balancing in accordance with some embodiments discussed herein.

FIGS. 5A-5B provide operational examples of two unit-designation models in accordance with some embodiments discussed herein.

FIG. 6 provides an operational example of an operator-designation model in accordance with some embodiments discussed herein.

FIG. 7 provides an operational example of an operator cost-capacity model in accordance with some embodiments discussed herein.

FIG. 8 provides an operational example of an operational condition reward model in accordance with some embodiments discussed herein.

FIG. 9 provides an operational example of an operator-unit mapping arrangement in accordance with some embodiments discussed herein.

Figure 10:
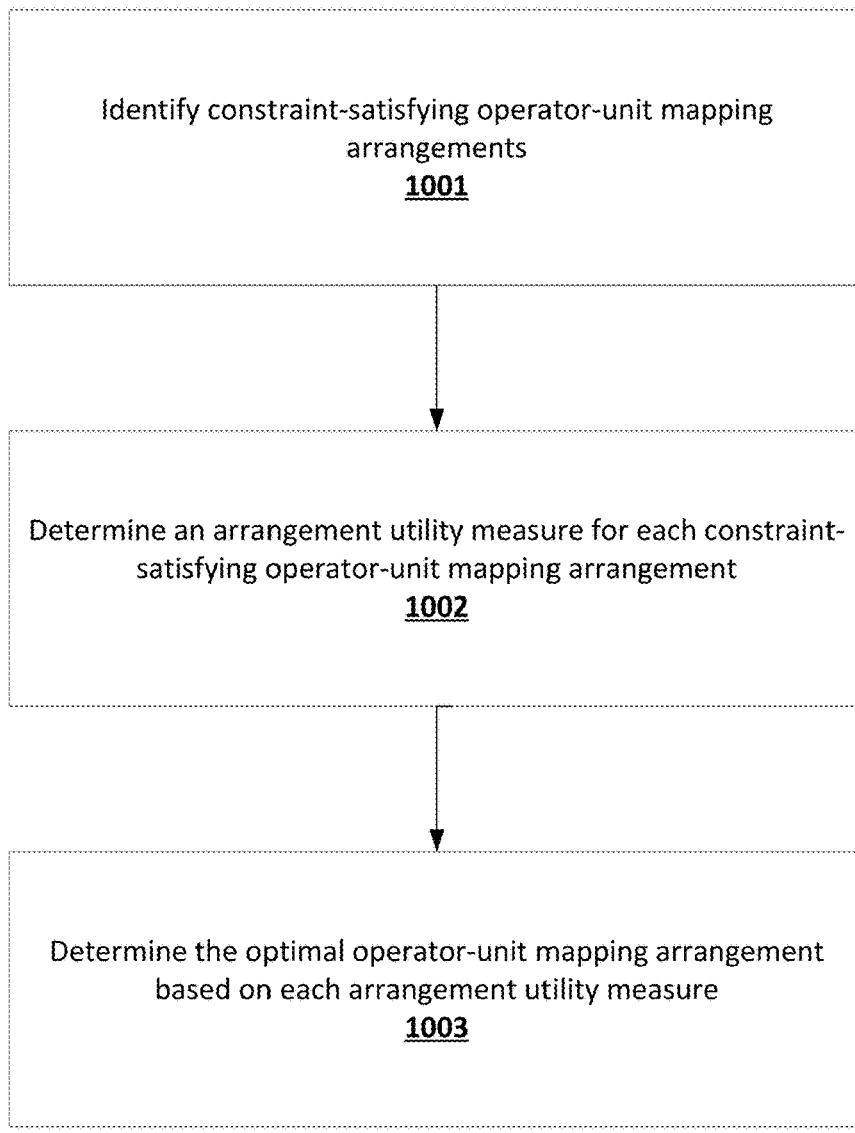

FIG. 10 is a flowchart diagram of an example process for generating an optimal operator-unit mapping arrangement in accordance with some embodiments discussed herein.

Figure 11:
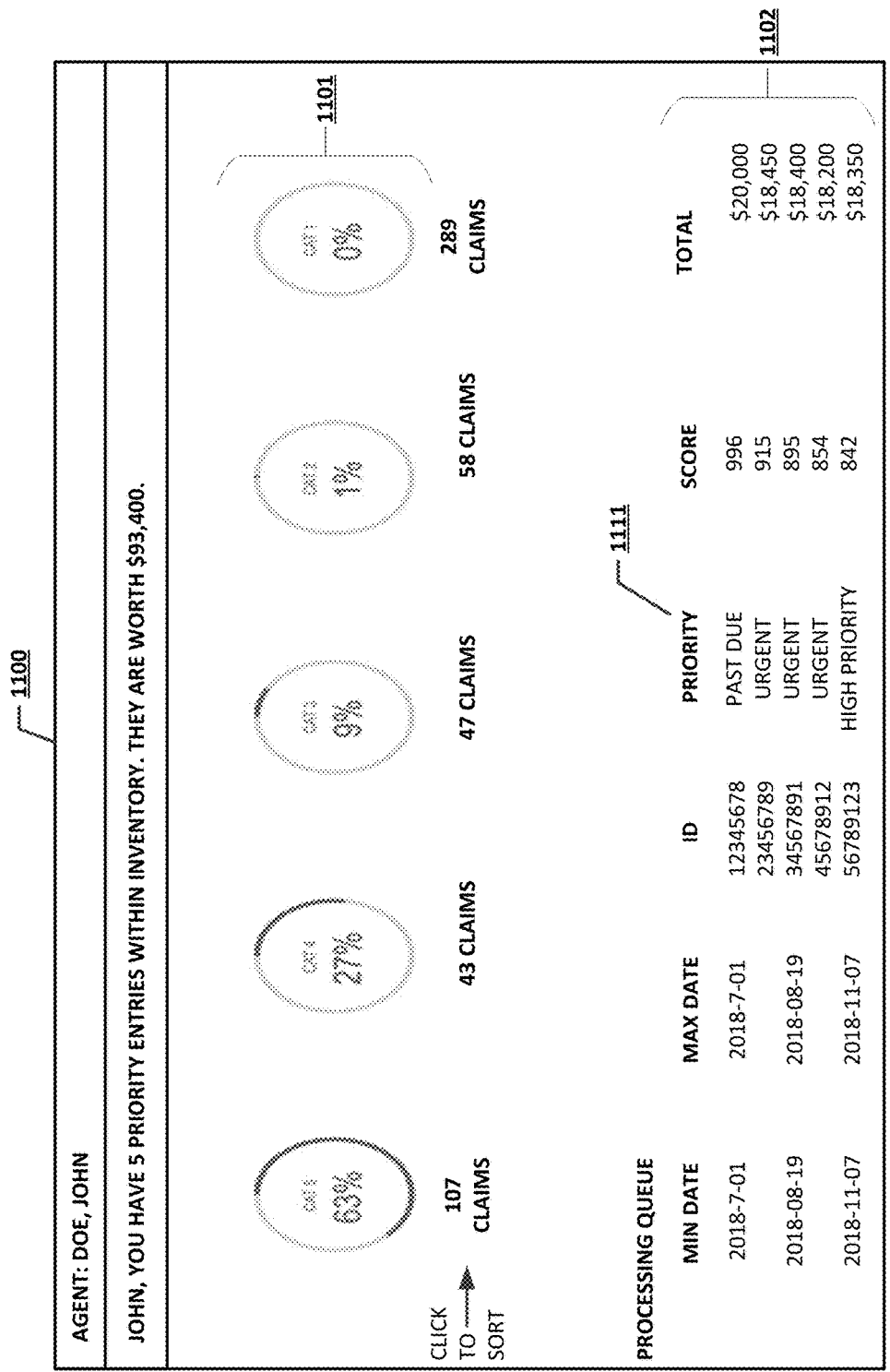

FIG. 11 provides an operational example of an operator queue user interface in accordance with some embodiments discussed herein.

Figure 12:
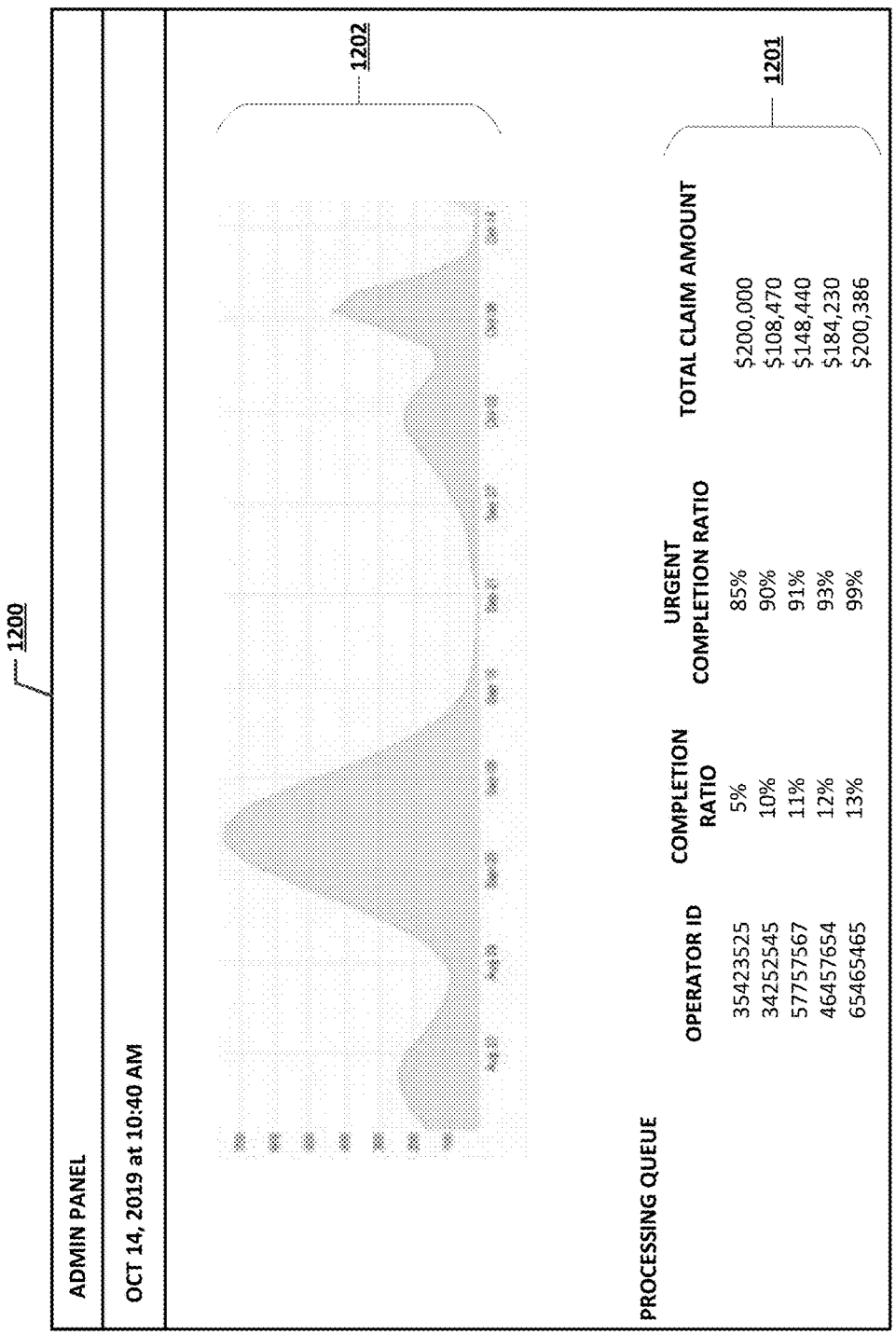

FIG. 12 provides an operational example of an operational load balancing administrator user interface in accordance with some embodiments discussed herein.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. OVERVIEW

Various embodiments of the present invention improve computational complexity and storage-wise efficiency of operational load balancing systems by decoupling constraint enforcement operations from the optimization operations along with comprehensive definition of desired constraint conditions when performing constrained-optimization-based operational load balancing. For example, various embodiments of the present invention can efficiently perform constrained operational load balancing on a filtered subset of operator-unit mapping arrangements that satisfy an operator unity constraint and an operator capacity constraint, rather than on all possible operator-unit mapping arrangements, an action that in effect results in decoupling of constraint enforcement operations from the optimization operations. By decoupling constraint enforcement operations from the optimization operations, various embodiments of the present invention reduce the computational cost of performing the optimization operations as well as the amount of storage resources needed to store the input data for the optimization operations. Thus, by introducing techniques for decoupling of constraint enforcement operations from the optimization operations along with comprehensive definition of desired constraint conditions when performing constrained-optimization-based operational load balancing, various embodiments of the present invention make important technical contributions to the field of operational load balancing through improving computational complexity and storage-wise efficiency of operational load balancing systems.

Moreover, various embodiments of the present invention improve computational efficiency and operational reliability of performing operational load balancing operations by determining an optimal mapping between operator profiles and work unit profiles prior to determining priority scores for work unit profiles. This in turn enables an operational load balancing system to reduce the number of work unit profiles for which priority scores need to be generated, as work unit profiles not assigned by the optimal mapping do not need to be assigned priority scores immediately. This in turn reduces the scale of work unit prioritization operations performed by operational load balancing systems and in turn reduces the effect of a major efficiency and accuracy bottleneck for many existing operational load balancing systems. Thus, by determining an optimal mapping between operator profiles and work unit profiles prior to determining priority scores for work unit profiles, various embodiments of the present invention make additional important technical contributions to the field of operational load balancing by improving computational complexity and storage-wise efficiency of operational load balancing systems.

II. EXEMPLARY DEFINITIONS

The term "work unit profile" may refer to a data object that describes an action item that an operational system is tasked to perform. For example, if the operational system is a medical provider system (e.g., a hospital system), the work unit profile may describe a medical action (e.g., a magnetic resonance imaging (MRI) action, a lab test performance action, a drug prescription action, a medical visit action, and/or the like) that the medical provider system is tasked to perform. As another example, if the operational system is a health insurance provider system, the work unit profile may describe a claim processing action (e.g., a claim review action, a claim audit action, a claim examination action, a claim approval action, and/or the like) or a medical record processing action (e.g., a medical chart review actions, such as a medical chart review action of a medical chart that may be performed to determine whether a health insurance claim corresponding to the corresponding medical chart constitutes an overpaid health insurance claim). As yet another example, if the operational system is a software system, the work unit profile may describe a set of software operations (e.g., a set of rate-limiting operations) configured to be performed by the operational system.

The term "operational condition designation" may refer to a data object that describes a real-world condition that can be addressed by performing action items described by one or more related work unit profiles. For example, if work unit profiles describe medical actions, the operational condition designations may describe medical conditions that the medical actions may be configured to address (e.g., to address medical condition A, work units B-C may be deemed effective). As another example, if work unit profiles describe health insurance claim processing actions, the operational condition designations may describe medical conditions that relate to claims being processed by the health insurance claim processing actions (e.g., medical claim D may be related to medical conditions E-F). As yet another example, if work unit profiles describe medical record processing actions, the operational condition designations may describe medical conditions that the underlying medical records document (e.g., medical record G documents occurrence of medical conditions H-I in a particular patient). As a further example, if work unit profiles describe health insurance claim processing actions, the operational condition designations may describe claim types of the underlying health insurance claims (e.g., health insurance claim J is a low-value claim, an elderly-patient claim, and/or the like). As an additional example, if work unit profile describes software operation sets, the operational condition designations may describe action types and/or resource-cost-intensity labels for the noted software operation sets.

The term "operator profile" may refer to a data object that describes an entity associated with an operational system that may be tasked to perform work unit profiles. For example, if the operational system is a medical provider system (e.g., a hospital system), the operator profile may describe a medical provider and/or a medical provider subsystem (e.g., a lab department) associated with the medical provider system. As another example, if the operational system is a health insurance claim processing system, the operator profile may describe a health insurance claim examiner associated with the health insurance claim processing system, a health insurance claim auditor associated with the health insurance claim processing system, a health insurance claim evaluator associated with the health insurance claim processing system, and/or the like. As yet another example, if the operational system is a software system, the operator profile may describe a particular software component (e.g., a rate-limiting software component) within the software system.

The term "unit-designation model" may refer to a data object that describes a unit-designation effectiveness measure for each unit-designation pair of a plurality of unit-designation pairs that comprises a work unit profile of the plurality of work unit profiles associated with an operational system and an operational condition designation of the one or more operational condition designations associated with an operational system. In some of the noted embodiments, the unit-designation effectiveness measure for a unit-designation pair describes estimated effectiveness of performing the work unit profile that is associated with the unit designation pair to addressing the operational condition designation that is associated with the operator-designation pair. For example, given an operational system that is associated with work unit profiles W1 and W2 as well as operational condition designations D1 and D2, the unit-designation model may describe that: (i) the work unit profile W1 is estimated to be 80% effective to addressing the operational condition designation D1, (ii) the work unit profile W2 is estimated to be 1% effective to addressing the operational condition designation D1, (iii) the work unit profile W1 is estimated to be 2% effective to addressing the operational condition designation D1, (iv) the work unit profile W2 is estimated to be 99% effective to addressing the operational condition designation D2. In some embodiments, the unit-designation model describes at least one estimated operator-designation effectiveness of a corresponding work unit profile and a corresponding operational condition designation as a probability distribution (i.e., as an "operator-designation probability distribution," as referred to herein). For example, the unit-designation model may describe that the work unit profile W1 is likely to be 50%-70% effective to address operational condition designation D1 with a 10% confidence, that the work unit profile W1 is likely to be 70%-85% effective to address operational condition designation D1 with a 80% confidence, and that the work unit profile W1 is likely to be 85%-100% effective to address operational condition designation D1 with a 10% confidence.

The term "operator-designation model" may refer to a data object that describes an operator-designation effectiveness measure for each operator-designation pair of a plurality of operator-designation pairs that comprises an operator profile of the plurality of operator profiles associated with an operational system and an operational condition designation of the one or more operational condition designations associated with an operational system. In some of the noted embodiments, the operator-designation effectiveness measure for an operator-designation pair describes estimated effectiveness (e.g., an estimated expertise of, yield of, and/or quality of) utilizing the operator profile that is associated with the operator designation pair to addressing the operational condition designation that is associated with the operator-designation pair. For example, given an operational system that is associated with operator profiles O1 and O2 as well as operational condition designations D1 and D2, the operator-designation model may describe that: (i) utilizing the operator profile O1 is estimated to be 80% effective to addressing the operational condition designation D1, (ii) utilizing the operator profile O2 is estimated to be 12% effective to addressing the operational condition designation D1, (iii) utilizing the operator profile O1 is estimated to be 23% effective to addressing the operational condition designation D1, (iv) utilizing the operator profile O2 is estimated to be 55% effective to addressing the operational condition designation D2. In some embodiments, the operator-designation model describes at least one estimated operator-designation effectiveness of a corresponding operator profile and a corresponding operational condition designation as a probability distribution (i.e., as an "operator-designation probability distribution," as referred to herein). For example, the operator-designation model may describe that utilizing the operator profile O1 is likely to be 50%-70% effective to address operational condition designation D1 with a 10% confidence, that utilizing the operator profile O1 is likely to be 70%-85% effective to address operational condition designation D1 with a 80% confidence, and that utilizing the operator profile O1 is likely to be 85%-100% effective to address operational condition designation D1 with a 10% confidence.

The term "operator cost-capacity model" may refer to a data object that describes an estimated per-time-unit cost of utilizing a corresponding operator profile as well as an estimated total time capacity of utilizing the corresponding operator profile. For example, the operator cost-capacity model for a medical provider may describe an hourly cost of utilizing the medical provider as well as the estimated total number of hours of availability of the medical provider during a particular time window. As another example, the operator cost-capacity model for a claim processing agent may describe an hourly cost of utilizing the claim processing agent as well as the estimated total number of hours of availability of the claim processing agent during a particular time window. As yet another example, the operator cost-capacity model for a software system component may describe a per-time-unit cost of performing operations of the software system component as well as the total time of the availability of the software system component during a current time window. In some embodiments, the cost measures described by the operator cost-capacity model may be determined based on at least one of: (i) one or more cost measure determination rules, (ii) the output of a machine learning model configured to process historical data about estimated costs of utilizing particular operator profiles, and (iii) subject matter domain data about estimated costs of utilizing particular operator profiles.

In some embodiments, at least one cost measure described by the operator cost-capacity model may be a probability distribution (referred to as an "operator cost probability distribution" herein). For example, the operator cost-capacity model may describe that the estimated per-time-unit cost for a particular operator profile is $95-$100 with a confidence of 10%, that the estimated per-time-unit cost for the particular operator profile is $100-$200 with a confidence of 80%, and that the estimated per-time-unit cost for the particular operator profile is $200-$400 with a confidence of 10%. In some embodiments, at least one capacity measure described by the operator cost-capacity model may be a probability distribution (referred to as an "operator capacity probability distribution" herein). For example, the operator cost-capacity model may describe that the estimated time capacity for a particular operator profile is 1-5 hours with a confidence of 10%, that the estimated time capacity for the particular operator profile is 5-8 hours with a confidence of 80%, and that the estimated time capacity for the particular operator profile is 8-10 hours with a confidence of 10%.

The term "operational condition reward model" may refer to a data object that describes an estimated reward of effectively addressing each operational condition designation of the one or more operational condition designations associated with an operational system. For example, if the operational system is associated with operational condition designations O1-O2, the operational condition reward model may describe that the operational condition designation O1 has an estimated reward of $20 while performing the operational condition designation O2 has an estimated reward of $50. The estimated reward measure may be determined based on at least one of financial earning rewards, financial cost avoidance measures, reputational rewards, patient safety gains, and/or the like.

In some embodiments, at least one estimated reward by the operational condition reward model in relation to a corresponding operational condition designation is a probability distribution (e.g., a "an operational condition reward probability distribution," as referred to herein). For example, the operational condition reward model may describe that the estimated reward measure for operational condition designations O1 is $5-$10 with a confidence of 10%, that the estimated reward measure for operational condition designations O1 is $10-$20 with a confidence of 80%, and that the estimated reward measure for operational condition designations O1 is $20-$40 with a confidence of 10%. In some embodiments, the reward measures described by the operational condition reward model may be determined based on at least one of: (i) one or more reward measure determination rules, (ii) the output of a machine learning model configured to process historical data about estimated rewards of successfully addressing operational condition designations, and (iii) subject matter domain data about estimated rewards of successfully addressing operational condition designations.

The term "operator-unit mapping arrangement" may refer to a data object that describes a mapping (e.g., a one-to-one mapping and/or a one-to-many mapping) of the plurality of work unit profiles associated with an operational system to the plurality of operator profiles associated with the operational system. For example, given an operational system that is associated with work unit profiles W1-W2 as well as operator profiles O1-O2, example operator-unit mapping arrangements for the operational system include an operator-unit mapping arrangement that describes the mapping {W1→O1 and W2→O2}, an operator-unit mapping arrangement that describes the mapping {W1→O1 and W2→O1}, and/or the like.

The term "arrangement utility measure" may refer to a data object that describes values that describe an estimated utility of performing load balancing operations for an operational system based on a corresponding operator-unit mapping arrangement. For example, each arrangement utility measure for an operator-unit mapping arrangement may be an arrangement utility value that describes an estimated utility of performing load balancing operations for an operational system based on the mappings of the noted operator-unit mapping arrangement. As another example, each arrangement utility measure for an operator-unit mapping arrangement may be a stochastic arrangement utility measure for the operator-unit mapping arrangement, such as a stochastic arrangement utility measure that describes at least one of (e.g., all of) each operator-designation probability distribution that is described by an operator-designation model for the operational system, each unit-designation probability distribution that is described by an unit-designation model for the operational system, each operational condition reward distribution described by an operational condition reward model for the operational system, each operator cost probability distribution that is described by an operator cost-capacity model for the operational system, and each operator capacity probability distribution that is described by the operator cost-capacity model for the operational system.

The term "optimization-based ensemble machine learning model" may refer to a data object that describes parameters and/or hyper-parameters of a machine learning model that is configured to: (i) process values/distributions related to various operator-unit mapping arrangements that are obtained from a plurality of data models in order to generate an arrangement utility measure for each operator-unit mapping arrangement, and (ii) determine an optimal operator-unit mapping arrangement from the various operator-unit mapping arrangements based on each arrangement utility measure for an operator-unit mapping arrangement. In some embodiments, the optimization-based ensemble machine learning model is a linear optimization model. In some embodiments, the optimization-based ensemble machine learning model is a deterministic optimization model, e.g., a deterministic optimization model that is configured to generate arrangement utility values for operator-unit mapping arrangements and process the arrangement utility values in order to determine an optimal operator-unit mapping arrangement. In some embodiments, the optimization-based ensemble machine learning model is a stochastic optimization model, e.g., a stochastic optimization model that is configured to generate stochastic arrangement utility measures for operator-unit mapping arrangements and process the stochastic arrangement utility measures in order to determine an optimal operator-unit mapping arrangement. The optimization tasks performed by the optimization-based ensemble machine learning model may include one or more maximization tasks (e.g., if the arrangement utility measures describe arrangement reward measures for operator-unit mapping arrangements) and/or one or more minimization tasks (e.g., if the arrangement utility measures describe arrangement cost/loss measures for operator-unit mapping arrangements).

The term "constraint-satisfying operator-unit mapping arrangement" may refer to a data object that describes an operator-unit mapping arrangement that satisfies (i.e., does not fail the tests defined by) one or more desired constraint conditions. Examples of desired constraint conditions include an operator unity constraint and an operator capacity constraint, which are described in greater detail below. However, while various embodiments of the present invention are discussed with reference to imposing an operator unity constraint and an operator capacity constraint, a person of ordinary skill in the relevant technology will recognize that other constraint conditions may be enforced instead of and/or in addition to at least one of the operator unity constraint and the operator capacity constraint. For example, in some embodiments, the desired constraint conditions may include a constraint condition requiring that each work unit profile is assigned to at least one operator provider. As another example, in some embodiments, the desired constraint conditions may include a constraint condition requiring that each operator profile is assigned to at least one work unit profile.

The term "operator unity constraint" may refer to a data object that describes a constraint condition requiring that an operator-unit mapping arrangement maps each work unit of the plurality of work units associated with an operational system to no more than one operator profile of the plurality of operator profiles associated with the operational system. For example, given an operational system that is associated with work unit profiles W1-W2 as well as operator profiles O1-O2, the following operator-unit mapping arrangements satisfy the operator unity constraint: {W1→O1, W2→O2}, {W1→O1, W2→O1}, and {W1→O2, W2→O2}. However, given an operational system that is associated with work unit profiles W1-W2 as well as operator profiles O1-O2, the following operator-unit mapping arrangements fail to satisfy the operator unity constraint: {W1→O1, W1→O2, W2→O1} and {W1→O2, W2→O1, W2→O2}. In some embodiments, the requirements of the operator unity constraint may correspond to the requirement of Equation 3 of the present document, which is reproduced and described below. The term "operator capacity constraint" may refer to a data object that describes a constraint condition requiring that the total operator utilization measure of each operator profile of the plurality of operator profiles under an operator-unit mapping arrangement satisfies (e.g., does not exceed) the estimated capacity of the operator profile, where the total operator utilization measure of an operator profile under the operator-unit mapping arrangement is a measure of a total time that the operator profile is expected to spend in order to perform the work unit profiles assigned to the operator profile under the operator-unit mapping arrangement. The operator capacity constraint is thus only satisfied if each operator profile is expected to be utilized at or below capacity. In some embodiments, the total operator utilization measure of an operator profile under an operator-unit mapping arrangement that is used to determine whether the operator-unit mapping arrangement satisfies operator capacity constraint is determined based on the number of work units assigned to the operator profile as well as the expected time that the operator profile is expected to take to perform a work unit profile (e.g., an average/median/modal time determined based on historical work unit performance data associated with the operator profiles, an average/median/modal time determined based on historical work unit performance data associated with a population of operator profiles that includes the particular operator profile, and/or the like). In some embodiments, the requirements of the operator capacity constraint may correspond to the requirement of Equation 2 of the present document, which is reproduced and described below.

III. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a dataset query or search language, and/or a report writing language. In one or more example embodiments, a software component comprising instructions in one of the foregoing examples of programming languages may be executed directly by an operating system or other software components without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations. Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. EXEMPLARY SYSTEM ARCHITECTURE

FIG. 1 is a schematic diagram of an example architecture 100 for performing constrained-optimization-based operational load balancing. The architecture 100 includes an operational load balancing system 101 configured to perform operational load balancing operations in relation to one or more operational systems in order to generate operational load balancing outputs and present the operational load balancing outputs to one or more client computing devices 102 (e.g., client computing entities 102 associated with operator profiles of the noted operational systems, client computing entities 102 associated with administrative profiles of the noted operational systems, and/or the like).

In some embodiments, the operational load balancing system 101 may communicate with at least one of the client computing entities 102 and/or at least one of the sensor computing entities 105 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The operational load balancing system 101 includes an operational load balancing computing entity 106 and a storage subsystem 108. The operational load balancing computing entity 106 may be configured to perform the constrained-optimization-based operational load balancing operations of the present invention, for example according to at least some of the techniques described with reference to FIGS. 4-12 below.

The storage subsystem 108 may be configured to store configuration data and/or input data utilized by the operational load balancing computing entity 106 to perform constrained-optimization-based operational load balancing. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Furthermore, each storage unit in the storage subsystem 108 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Operational Load Balancing Computing Entity

FIG. 2 provides a schematic of an operational load balancing computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the operational load balancing computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the operational load balancing computing entity 106 may include or be in communication with one or more processing elements 205 (also referred to as processors, processing circuitry, and/or similar terms used herein interchangeably) that communicate with other elements within the operational load balancing computing entity 106 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the operational load balancing computing entity 106 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store datasets, dataset instances, dataset management systems, data, applications, programs, program modules, scripts, source code, object code, byte code, compiled code, interpreted code, machine code, executable instructions, and/or the like. The term dataset, dataset instance, dataset management system, and/or similar terms used herein interchangeably may refer to a collection of records or data that is stored in a computer-readable storage medium using one or more dataset models, such as a hierarchical dataset model, network model, relational model, entity-relationship model, object model, document model, semantic model, graph model, and/or the like.

In one embodiment, the operational load balancing computing entity 106 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the datasets, dataset instances, dataset management systems, data, applications, programs, program modules, scripts, source code, object code, byte code, compiled code, interpreted code, machine code, executable instructions, and/or the like being executed by, for example, the processing element 205. Thus, the datasets, dataset instances, dataset management systems, data, applications, programs, program modules, scripts, source code, object code, byte code, compiled code, interpreted code, machine code, executable instructions, and/or the like may be used to control certain aspects of the operation of the operational load balancing computing entity 106 with the assistance of the processing element 205 and operating system.

As indicated, in one embodiment, the operational load balancing computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the operational load balancing computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the operational load balancing computing entity 106 may include or be in communication with one or more input elements, such as a keyboard input, a mouse input, a touch screen/display input, motion input, movement input, audio input, pointing device input, joystick input, keypad input, and/or the like. The operational load balancing computing entity 106 may also include or be in communication with one or more output elements (not shown), such as audio output, video output, screen/display output, motion output, movement output, and/or the like.

Exemplary Client Computing Entity

FIG. 3 provides an illustrative schematic representative of a client computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Client computing entities 102 can be operated by various parties. As shown in FIG. 3, the client computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the client computing entity 102 may be capable of operating with one or more air interface standards, communication protocols, modulation types, and access types. More particularly, the client computing entity 102 may operate in accordance with any of a number of wireless communication standards and protocols, such as those described above with regard to the operational load balancing computing entity 106. In a particular embodiment, the client computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the client computing entity 102 may operate in accordance with multiple wired communication standards and protocols, such as those described above with regard to the operational load balancing computing entity 106 via a network interface 320.

Via these communication standards and protocols, the client computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The client computing entity 102 can also download changes, add-ons, and updates, for instance, to its firmware, software (e.g., including executable instructions, applications, program modules), and operating system.

According to one embodiment, the client computing entity 102 may include location determining aspects, devices, modules, functionalities, and/or similar words used herein interchangeably. For example, the client computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the client computing entity's 102 position in connection with a variety of other systems, including cellular towers, Wi-Fi access points, and/or the like. Similarly, the client computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The client computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the client computing entity 102 to interact with and/or cause display of information/data from the operational load balancing computing entity 106, as described herein. The user input interface can comprise any of a number of devices or interfaces allowing the client computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the client computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The client computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store datasets, dataset instances, dataset management systems, data, applications, programs, program modules, scripts, source code, object code, byte code, compiled code, interpreted code, machine code, executable instructions, and/or the like to implement the functions of the client computing entity 102. As indicated, this may include a user application that is resident on the entity or accessible through a browser or other user interface for communicating with the operational load balancing computing entity 106 and/or various other computing entities.

In another embodiment, the client computing entity 102 may include one or more components or functionality that are the same or similar to those of the operational load balancing computing entity 106, as described in greater detail above. As will be recognized, these architectures and descriptions are provided for exemplary purposes only and are not limiting to the various embodiments.

In various embodiments, the client computing entity 102 may be embodied as an artificial intelligence (AI) computing entity, such as an Amazon Echo, Amazon Echo Dot, Amazon Show, Google Home, and/or the like. Accordingly, the client computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. EXEMPLARY SYSTEM OPERATIONS

FIG. 4 is a flowchart diagram of an example process 400 for performing constrained-optimization-based operational load balancing for an operational system that is associated with a plurality of operator profiles, a plurality of work unit profiles, and one or more operational condition designations. Via the various steps/operations of the process 400, the operational load balancing computing entity 106 can efficiently perform constrained operational load balancing on a filtered subset of operator-unit mapping arrangements that satisfy an operator unity constraint and an operator capacity constraint, rather than on all possible operator-unit mapping arrangements. By decoupling of constraint enforcement operations from the optimization operations along with comprehensive definition of desired constraint conditions, various embodiments of the present invention reduce the computational cost of performing the optimization operations as well as the amount of storage resources needed to store the input data for the optimization operations.

The process 400 begins at step/operation 401 when the operational load balancing computing entity 106 retrieves (e.g., from the storage subsystem 108) a unit-designation model that describes relationships between the plurality of work unit profiles and the plurality of operational condition designations. Aspects of work unit profiles, operational condition designations, and unit-designation models are described in greater detail below.

In some embodiments, a work unit profile is a data object that describes an action item that an operational system is tasked to perform. For example, if the operational system is a medical provider system (e.g., a hospital system), the work unit profile may describe a medical action (e.g., an MRI action, a lab test performance action, a drug prescription action, a medical visit action, and/or the like) that the medical provider system is tasked to perform. As another example, if the operational system is a health insurance provider system, the work unit profile may describe a claim processing action (e.g., a claim review action, a claim audit action, a claim examination action, a claim approval action, and/or the like) or a medical record processing action (e.g., a medical chart review actions, such as a medical chart review action of a medical chart that may be performed to determine whether a health insurance claim corresponding to the corresponding medical chart constitutes an overpaid health insurance claim). As yet another example, if the operational system is a software system, the work unit profile may describe a set of software operations (e.g., a set of rate-limiting operations) configured to be performed by the operational system.

In some embodiments, an operational condition designation is a data object that describes a real-world condition that can be addressed by performing action items described by one or more related work unit profiles. For example, if work unit profiles describe medical actions, the operational condition designations may describe medical conditions that the medical actions may be configured to address (e.g., to address medical condition A, work units B-C may be deemed effective). As another example, if work unit profiles describe health insurance claim processing actions, the operational condition designations may describe medical conditions that relate to claims being processed by the health insurance claim processing actions (e.g., medical claim D may be related to medical conditions E-F). As yet another example, if work unit profiles describe medical record processing actions, the operational condition designations may describe medical conditions that the underlying medical records document (e.g., medical record G documents occurrence of medical conditions H-I in a particular patient). As a further example, if work unit profiles describe health insurance claim processing actions, the operational condition designations may describe claim types of the underlying health insurance claims (e.g., health insurance claim J is a low-value claim, an elderly-patient claim, and/or the like). As an additional example, if work unit profile describes software operation sets, the operational condition designations may describe action types and/or resource-cost-intensity labels for the noted software operation sets.

In some embodiments, a unit-designation model is a data object that describes a unit-designation effectiveness measure for each unit-designation pair of a plurality of unit-designation pairs that comprises a work unit profile of the plurality of work unit profiles associated with an operational system and an operational condition designation of the one or more operational condition designations associated with an operational system. In some of the noted embodiments, the unit-designation effectiveness measure for a unit-designation pair describes estimated effectiveness of performing the work unit profile that is associated with the unit designation pair to addressing the operational condition designation that is associated with the operator-designation pair. For example, given an operational system that is associated with work unit profiles W1 and W2 as well as operational condition designations D1 and D2, the unit-designation model may describe that: (i) the work unit profile W1 is estimated to be 80% effective to addressing the operational condition designation D1, (ii) the work unit profile W2 is estimated to be 1% effective to addressing the operational condition designation D1, (iii) the work unit profile W1 is estimated to be 2% effective to addressing the operational condition designation D1, (iv) the work unit profile W2 is estimated to be 99% effective to addressing the operational condition designation D2. In some embodiments, the unit-designation model describes at least one estimated operator-designation effectiveness of a corresponding work unit profile and a corresponding operational condition designation as a probability distribution (i.e., as an "operator-designation probability distribution," as referred to herein). For example, the unit-designation model may describe that the work unit profile W1 is likely to be 50%-70% effective to address operational condition designation D1 with a 10% confidence, that the work unit profile W1 is likely to be 70%-85% effective to address operational condition designation D1 with a 80% confidence, and that the work unit profile W1 is likely to be 85%-100% effective to address operational condition designation D1 with a 10% confidence.

In some embodiments, the unit-designation effectiveness measures described by the unit-designation model may be determined based on at least one of: (i) one or more unit-designation effectiveness rules, (ii) the output of a machine learning model configured to process historical data about correlations between work unit profiles and operational condition designations (e.g., historical data about whether particular medical operations have effectively addressed particular medical conditions, historical data about whether particular health insurance claim processing actions have effectively addressed issues pertaining to health insurance claims that relate to particular medical conditions, historical data about whether particular health insurance claim processing actions have effectively addressed issues pertaining to particular health insurance claim types, and/or the like), and (iii) subject matter domain data about correlations between work unit profiles and operational condition designations (e.g., subject matter domain data about whether particular medical operations have effectively addressed particular medical conditions, subject matter domain data about whether particular health insurance claim processing actions have effectively addressed issues pertaining to health insurance claims that relate to particular medical conditions, subject matter domain data about whether particular health insurance claim processing actions have effectively addressed issues pertaining to particular health insurance claim types, and/or the like).

Operational examples of unit-designation models are presented in FIGS. 5A-5B. As depicted in the unit designation model 500 of FIG. 5A: (i) the work unit profile 501 is related to the operational condition designation 511 with a unit-designation effectiveness measure of 79%, (ii) the work unit profile 501 is related to the operational condition designation 512 with a unit-designation effectiveness measure of 99%, and (iii) the work unit profile 502 is related to the operational condition designation 512 with a unit-designation effectiveness measure of 40%. Moreover, as depicted in the unit designation model 550 of FIG. 5B: (i) the work unit profile 551 is related to the operational condition designation 561 with a unit-designation effectiveness measure of 46%, (ii) the work unit profile 552 is related to the operational condition designation 562 with a unit-designation effectiveness measure of 88%, and (iii) the work unit profile 551 is related to the operational condition designation 561 with a unit-designation effectiveness measure of 39%.

Returning to FIG. 4, at step/operation 402, the operational load balancing computing entity 106 retrieves (e.g., from the storage subsystem 108) an operator-designation model that describes relationships between the plurality of operator profiles and the plurality of operational condition designations. Aspects of operator profiles and operator-designation models are described in greater detail below.

In some embodiments, an operator profile is a data object that describes an entity associated with an operational system that may be tasked to perform work unit profiles. For example, if the operational system is a medical provider system (e.g., a hospital system), the operator profile may describe a medical provider and/or a medical provider subsystem (e.g., a lab department) associated with the medical provider system. As another example, if the operational system is a health insurance claim processing system, the operator profile may describe a health insurance claim examiner associated with the health insurance claim processing system, a health insurance claim auditor associated with the health insurance claim processing system, a health insurance claim evaluator associated with the health insurance claim processing system, and/or the like. As yet another example, if the operational system is a software system, the operator profile may describe a particular software component (e.g., a rate-limiting software component) within the software system.

In some embodiments, an operator-designation model is a data object that describes an operator-designation effectiveness measure for each operator-designation pair of a plurality of operator-designation pairs that comprises an operator profile of the plurality of operator profiles associated with an operational system and an operational condition designation of the one or more operational condition designations associated with an operational system. In some of the noted embodiments, the operator-designation effectiveness measure for an operator-designation pair describes estimated effectiveness (e.g., an estimated expertise of, yield of, and/or quality of) utilizing the operator profile that is associated with the operator designation pair to addressing the operational condition designation that is associated with the operator-designation pair. For example, given an operational system that is associated with operator profiles O1 and O2 as well as operational condition designations D1 and D2, the operator-designation model may describe that: (i) utilizing the operator profile O1 is estimated to be 80% effective to addressing the operational condition designation D1, (ii) utilizing the operator profile O2 is estimated to be 12% effective to addressing the operational condition designation D1, (iii) utilizing the operator profile O1 is estimated to be 23% effective to addressing the operational condition designation D1, (iv) utilizing the operator profile O2 is estimated to be 55% effective to addressing the operational condition designation D2.

In some embodiments, the operator-designation model describes at least one estimated operator-designation effectiveness of a corresponding operator profile and a corresponding operational condition designation as a probability distribution (i.e., as an "operator-designation probability distribution," as referred to herein). For example, the operator-designation model may describe that utilizing the operator profile O1 is likely to be 50%-70% effective to address operational condition designation D1 with a 10% confidence, that utilizing the operator profile O1 is likely to be 70%-85% effective to address operational condition designation D1 with a 80% confidence, and that utilizing the operator profile O1 is likely to be 85%-100% effective to address operational condition designation D1 with a 10% confidence.

In some embodiments, the operator-designation effectiveness measures described by the operator-designation model may be determined based on at least one of: (i) one or more operator-designation effectiveness rules, (ii) the output of a machine learning model configured to process historical data about correlations between operator utilizations and operational condition designations (e.g., historical data about whether particular medical operators have effectively addressed particular medical conditions, historical data about whether particular health insurance claim processing agents have effectively addressed issues pertaining to health insurance claims that relate to particular medical conditions, historical data about whether particular health insurance claim processing agents have effectively addressed issues pertaining to particular health insurance claim types, and/or the like), and (iii) subject matter domain data about correlations between operator profiles and operational condition designations (e.g., subject matter domain data about whether particular medical professional categories have effectively addressed particular medical conditions, subject matter domain data about whether particular health insurance claim processing agent categories have effectively addressed issues pertaining to health insurance claims that relate to particular medical conditions, subject matter domain data about whether particular health insurance claim processing agent categories have effectively addressed issues pertaining to particular health insurance claim types, and/or the like).

An operational example of an operator-designation model 600 is depicted in FIG. 6. As depicted in FIG. 6, the operator-designation model 600 describes that the operator profile 601 is related to the operational condition designation 611 with a 90% probability. Moreover, as further depicted in FIG. 6, the operator-designation model 600 describes that the operator profile 602 is related to the operational condition designation 612 with a 20% probability.

Returning to FIG. 4, at step/operation 403, the operational load balancing computing entity 106 retrieves (e.g., from the storage subsystem 108) an operator cost-capacity model for each operator profile of the plurality of operator profiles. Aspects of operator cost-capacity models are described in greater detail below.

In some embodiments, an operator cost-capacity model is a data object that describes an estimated per-time-unit cost of utilizing a corresponding operator profile as well as an estimated total time capacity of utilizing the corresponding operator profile. For example, the operator cost-capacity model for a medical provider may describe an hourly cost of utilizing the medical provider as well as the estimated total number of hours of availability of the medical provider during a particular time window. As another example, the operator cost-capacity model for a claim processing agent may describe an hourly cost of utilizing the claim processing agent as well as the estimated total number of hours of availability of the claim processing agent during a particular time window. As yet another example, the operator cost-capacity model for a software system component may describe a per-time-unit cost of performing operations of the software system component as well as the total time of the availability of the software system component during a current time window.

In some embodiments, the cost measures described by the operator cost-capacity model may be determined based on at least one of: (i) one or more cost measure determination rules, (ii) the output of a machine learning model configured to process historical data about estimated costs of utilizing particular operator profiles, and (iii) subject matter domain data about estimated costs of utilizing particular operator profiles.

In some embodiments, at least one cost measure described by the operator cost-capacity model may be a probability distribution (referred to as an "operator cost probability distribution" herein). For example, the operator cost-capacity model may describe that the estimated per-time-unit cost for a particular operator profile is $95-$100 with a confidence of 10%, that the estimated per-time-unit cost for the particular operator profile is $100-$200 with a confidence of 80%, and that the estimated per-time-unit cost for the particular operator profile is $200-$400 with a confidence of 10%. In some embodiments, at least one capacity measure described by the operator cost-capacity model may be a probability distribution (referred to as an "operator capacity probability distribution" herein). For example, the operator cost-capacity model may describe that the estimated time capacity for a particular operator profile is 1-5 hours with a confidence of 10%, that the estimated time capacity for the particular operator profile is 5-8 hours with a confidence of 80%, and that the estimated time capacity for the particular operator profile is 8-10 hours with a confidence of 10%.

An operational example of an operator cost-capacity model 700 is depicted in FIG. 7. As depicted in FIG. 7, the operator cost-capacity model 700 describes that the operator profile 601 has a per-time-unit cost of $25 and a capacity of 39 time units within a current time window. As further depicted in FIG. 7, the operator cost-capacity model 700 describes that the operator profile 602 has a per-time-unit cost of $23 and a capacity of 47 time units within the current time window.

Returning to FIG. 4, at step/operation 404, the operational load balancing computing entity 106 retrieves (e.g., from the storage subsystem 108) an operational condition reward model for each work unit profile of the plurality of work unit profiles. Aspects of operational condition reward models are described in greater detail below.

In some embodiments, an operational condition reward model is a data object that describes an estimated reward of effectively addressing each operational condition designation of the one or more operational condition designations associated with an operational system. For example, if the operational system is associated with operational condition designations O1-O2, the operational condition reward model may describe that the operational condition designation O1 has an estimated reward of $20 while performing the operational condition designation O2 has an estimated reward of $50. The estimated reward measure may be determined based on at least one of financial earning rewards, financial cost avoidance measures, reputational rewards, patient safety gains, and/or the like.

In some embodiments, at least one estimated reward by the operational condition reward model in relation to a corresponding operational condition designation is a probability distribution (e.g., a "an operational condition reward probability distribution," as referred to herein). For example, the operational condition reward model may describe that the estimated reward measure for operational condition designations O1 is $5-$10 with a confidence of 10%, that the estimated reward measure for operational condition designations O1 is $10-$20 with a confidence of 80%, and that the estimated reward measure for operational condition designations O1 is $20-$40 with a confidence of 10%. In some embodiments, the reward measures described by the operational condition reward model may be determined based on at least one of: (i) one or more reward measure determination rules, (ii) the output of a machine learning model configured to process historical data about estimated rewards of successfully addressing operational condition designations, and (iii) subject matter domain data about estimated rewards of successfully addressing operational condition designations.

An operational example of an operational condition reward model 800 is depicted in FIG. 8. As depicted in FIG. 8, the operational condition reward model 800 describes that effectively addressing the operational condition designation 801 has an estimated reward of $2500. Moreover, as further As depicted in FIG. 8, the operational condition reward model 800 describes that effectively addressing the operational condition designation 802 has an estimated reward of $1500.

Returning to FIG. 4, at step/operation 405, the operational load balancing computing entity 106 determines an optimal operator-unit mapping arrangement based on the unit-designation model, the operator-designation model, the operational condition reward model, and the operator cost-capacity model. In some embodiments, to determine the optimal operator-unit mapping arrangement, the operational load balancing computing entity 106 performs an optimization operation (e.g., a linear optimization operation, a deterministic optimization operation, and/or a stochastic optimization operation) by processing values/distributions determined based on at least one of the unit-designation model, the operator-designation model, the operational condition reward model, and the operator cost-capacity model using an optimization-based ensemble machine learning model. Aspects of operator-unit mapping arrangements, optimal operator-unit mapping arrangements, and optimization-based ensemble machine learning models are described in greater detail below.

In some embodiments, an operator-unit mapping arrangement is a data object that describes a mapping (e.g., a one-to-one mapping and/or a one-to-many mapping) of the plurality of work unit profiles associated with an operational system to the plurality of operator profiles associated with the operational system. For example, given an operational system that is associated with work unit profiles W1-W2 as well as operator profiles O1-O2, example operator-unit mapping arrangements for the operational system include an operator-unit mapping arrangement that describes the mapping {W1→O1 and W2→O2}, an operator-unit mapping arrangement that describes the mapping {W1→O1 and W2→O1}, and/or the like. An operational example of an operator-unit mapping arrangement 900 is depicted in FIG. 9. As depicted in FIG. 9, the operator-unit mapping arrangement describes that the operator profile 601 is mapped to the work unit profiles 911-912, while the operator profile 602 is mapped to the work unit profiles 913-914.

In some embodiments, values/distributions associated with an operator-unit mapping arrangement (e.g., values/distributions determined based on at least one of an unit-designation model, an operator-designation model, an operational condition reward model, and an operator cost-capacity model) may be processed to determine an arrangement utility measure for the operator-unit mapping arrangement.

In some embodiments, an arrangement utility measure is a data object that describes values indicating an estimated utility of performing load balancing operations for an operational system based on a corresponding operator-unit mapping arrangement. For example, each arrangement utility measure for an operator-unit mapping arrangement may be an arrangement utility value that describes an estimated utility of performing load balancing operations for an operational system based on the mappings of the noted operator-unit mapping arrangement.

In some embodiments, each arrangement utility measure for an operator-unit mapping arrangement may be a stochastic arrangement utility measure for the operator-unit mapping arrangement, such as a stochastic arrangement utility measure that describes at least one of (e.g., all of) each operator-designation probability distribution that is described by an operator-designation model for the operational system, each unit-designation probability distribution that is described by an unit-designation model for the operational system, each operational condition reward distribution described by an operational condition reward model for the operational system, each operator cost probability distribution that is described by an operator cost-capacity model for the operational system, and each operator capacity probability distribution that is described by the operator cost-capacity model for the operational system.

In some embodiments, an optimization-based ensemble machine learning model is a data object that describes parameters and/or hyper-parameters of a machine learning model that is configured to: (i) process values/distributions related to various operator-unit mapping arrangements that are obtained from a plurality of data models in order to generate an arrangement utility measure for each operator-unit mapping arrangement, and (ii) determine an optimal operator-unit mapping arrangement from the various operator-unit mapping arrangements based on each arrangement utility measure for an operator-unit mapping arrangement.

In some embodiments, the optimization-based ensemble machine learning model is a linear optimization model. In some embodiments, the optimization-based ensemble machine learning model is a deterministic optimization model, e.g., a deterministic optimization model that is configured to generate arrangement utility values for operator-unit mapping arrangements and process the arrangement utility values in order to determine an optimal operator-unit mapping arrangement. In some embodiments, the optimization-based ensemble machine learning model is a stochastic optimization model, e.g., a stochastic optimization model that is configured to generate stochastic arrangement utility measures for operator-unit mapping arrangements and process the stochastic arrangement utility measures in order to determine an optimal operator-unit mapping arrangement. The optimization tasks performed by the optimization-based ensemble machine learning model may include one or more maximization tasks (e.g., if the arrangement utility measures describe arrangement reward measures for operator-unit mapping arrangements) and/or one or more minimization tasks (e.g., if the arrangement utility measures describe arrangement cost/loss measures for operator-unit mapping arrangements).

In some embodiments, performing the operations of the optimization-based ensemble machine learning model includes maximizing arrangement utility measures for various constraint-satisfying operator-unit mapping arrangements, where the maximizing arrangement utility measures are determined using the Equation 1 and the constraint-satisfying operator-unit mapping arrangements are determined based on at least one of the constraint of Equation 2 and the constraint of Equation 3:

$$\sum_{\substack{i \in I \\ h \in H \\ k \in K}} V_h P_{ih} Q_{hk} R_{ik} - \sum_{\substack{i \in I \\ k \in K}} R_{ik} S_k M_k \qquad \text{Equation 1}$$

$$\sum_{i \in I} R_{ik} M_k \leq T_k \forall\, k \in K \qquad \text{Equation 2}$$

$$\sum_{k \in K} R_{ik} \leq 1 \forall\, i \in I \qquad \text{Equation 3}$$

In Equations 1-3: (i) i is an index value that iterates over the set I, which includes the plurality of work unit profiles; (ii) k is an index value that iterates over the set K, which includes the plurality of operator profiles; (iii) h is an index value that iterates over the set H, which includes the one or more operational condition designations; (iv) $V_h$ describes the estimated reward measure for effectively addressing the operational condition designation h, as determined based on the operational condition reward model; (v) $P_{ih}$ describes the unit-designation effectiveness measure for the work unit profile i and the operational condition designation h, which may be a value that is selected from a bounded range (e.g., a value bounded by [0,1], a value bounded by [0%-100%], and/or the like); (vi) $Q_{hk}$ describes the operational-designation effectiveness measure for the operator profile h and the operational condition designation h, which may be a value that is selected from a bounded range (e.g., a value bounded by [0,1], a value bounded by [0%-100%], and/or the like); (vii) $M_k$ describes an expected time that the operator profile k may consume to perform a work unit profile; (viii) $S_k$ describes the estimated per-time-unit cost of utilizing the operator profile k, as determined based on the operator cost-capacity model; (ix) $R_{ik}$ describes a binary value denoting whether the operator profile k is mapped to the work unit profile i under a particular operator-unit mapping arrangement being processed by the optimization-based ensemble machine learning model; and (x) $S_k$ describes the estimated capacity of the operator profile k, as determined based on the operator cost-capacity model.

In some embodiments, step/operation 405 may be performed in accordance with the process depicted in FIG. 10. The process depicted in FIG. 10 begins at step/operation 1001 when the operational load balancing computing entity 106 identifies a plurality of constraint-satisfying operator-unit mapping arrangements. In some embodiments, a constraint-satisfying operator-unit mapping arrangement is a data object that describes an operator-unit mapping arrangement that satisfies (i.e., does not fail the tests defined by) one or more desired constraint conditions. Examples of desired constraint conditions include an operator unity constraint and an operator capacity constraint, which are described in greater detail below. However, while various embodiments of the present invention are discussed with reference to imposing an operator unity constraint and an operator capacity constraint, a person of ordinary skill in the relevant technology will recognize that other constraint conditions may be enforced instead of and/or in addition to at least one of the operator unity constraint and the operator capacity constraint. For example, in some embodiments, the desired constraint conditions may include a constraint condition requiring that each work unit profile is assigned to at least one operator provider. As another example, in some embodiments, the desired constraint conditions may include a constraint condition requiring that each operator profile is assigned to at least one work unit profile.

In some embodiments, an operator unity constraint is a data object that describes a constraint condition requiring that an operator-unit mapping arrangement maps each work unit of the plurality of work units associated with an operational system to no more than one operator profile of the plurality of operator profiles associated with the operational system. For example, given an operational system that is associated with work unit profiles W1-W2 as well as operator profiles O1-O2, the following operator-unit mapping arrangements satisfy the operator unity constraint: {W1→O1, W2→O2}, {W1→O1, W2→O1}, and {W1→O2, W2→O2}. However, given an operational system that is associated with work unit profiles W1-W2 as well as operator profiles O1-O2, the following operator-unit mapping arrangements fail to satisfy the operator unity constraint: {W1→O1, W1→O2} and {W2→O1, W2→O2}. In some embodiments, the requirements of the operator unity constraint may correspond to the requirement of Equation 3 of the present document.

In some embodiments, an operator capacity constraint is a data object that describes a constraint condition requiring that the total operator utilization measure of each operator profile of the plurality of operator profiles under an operator-unit mapping arrangement satisfies (e.g., does not exceed) the estimated capacity of the operator profile, where the total operator utilization measure of an operator profile under the operator-unit mapping arrangement is a measure of a total time that the operator profile is expected to spend in order to perform the work unit profiles assigned to the operator profile under the operator-unit mapping arrangement. The operator capacity constraint is thus only satisfied if each operator profile is expected to be utilized at or below capacity. In some embodiments, the total operator utilization measure of an operator profile under an operator-unit mapping arrangement that is used to determine whether the operator-unit mapping arrangement satisfies operator capacity constraint is determined based on the number of work units assigned to the operator profile as well as the expected time that the operator profile is expected to take to perform a work unit profile (e.g., an average/median/modal time determined based on historical work unit performance data associated with the operator profiles, an average/median/modal time determined based on historical work unit performance data associated with a population of operator profiles that includes the particular operator profile, and/or the like). In some embodiments, the requirements of the operator capacity constraint may correspond to the requirement of Equation 2 of the present document.

At operation 1002, the operational load balancing computing entity 106 determines an arrangement utility measure for each constraint-satisfying operator-unit mapping arrangement of the plurality of constraint-satisfying operator-unit mapping arrangements, where the arrangement utility measure for a constraint-satisfying operator-unit mapping arrangement describes an estimated utility of utilizing mappings between the plurality of operator profiles and the plurality of work unit profiles. In some embodiments, each arrangement utility measure for a constraint-satisfying operator-unit mapping arrangement of the plurality of constraint-satisfying operator-unit mapping arrangements is determined based on: (i) an operator-designation model that describes relationships between the plurality of operator profiles and the one or more operational condition designations, (ii) a unit-designation model that describes relationships between the plurality of work units and the one or more operational condition designations, (iii) an operational condition reward model that describes an estimated reward of each operational condition designation of the one or more operational condition designations, and (iv) an operator cost-capacity model that describes an estimated cost and the estimated capacity for each operator profile of the plurality of operator profiles.

In some embodiments, determining the arrangement utility measure for a constraint-satisfying operator-unit mapping arrangement of the plurality of constraint-satisfying operator-unit mapping arrangements comprises determining an arrangement reward measure for the constraint-satisfying operator-unit mapping arrangement based on the unit-designation model, the operator-designation model, and each operational condition reward model for a work unit profile of the plurality of work unit profiles; determining an arrangement cost measure for the constraint-satisfying operator-unit mapping arrangement based on each operator cost model for an operator profile of the plurality of operator profiles that is utilized by the constraint-satisfying operator-unit mapping arrangement; and determining the arrangement utility measure based on the arrangement reward measure and the arrangement cost measure. In some embodiments, generating an arrangement reward measure for a constraint-satisfying operator-unit mapping arrangement is determined using the operations of the first summation factor of the Equation 1 of the present document. In some embodiments, generating an arrangement cost measure for a constraint-satisfying operator-unit mapping arrangement is determined using the operations of the second summation factor of the Equation 1 of the present document. In some embodiments, generating an arrangement utility measure for a constraint-satisfying operator-unit mapping arrangement is determined using the operations of the Equation 1 of the present document.

At step/operation 1003, the operational load balancing computing entity 106 processes each arrangement utility measure for a constraint-satisfying operator-unit mapping arrangement of the plurality of constraint-satisfying operator-unit mapping arrangements using an optimization-based ensemble machine learning model to determine an optimal operator-unit mapping arrangement of the plurality of constraint-satisfying operator-unit mapping arrangements. In some embodiments, the operational load balancing computing entity 106 selects the constraint-satisfying operator-unit mapping arrangement whose arrangement utility measure is optimal (e.g., maximum or minimum) among all of the constraint-satisfying operator-unit mapping arrangements as the optimal operator-unit mapping arrangement. For example, if the arrangement utility measures are reward measures, the operational load balancing computing entity 106 may select the constraint-satisfying operator-unit mapping arrangement whose arrangement utility measure is maximal as the optimal operator-unit mapping arrangement. As another example, if the arrangement utility measures are cost/loss measures, the operational load balancing computing entity 106 may select the constraint-satisfying operator-unit mapping arrangement whose arrangement utility measure is minimal as the optimal operator-unit mapping arrangement.

Returning to FIG. 4, at step/operation 406, the operational load balancing computing entity 106 generates a priority score for each work unit profile that is assigned by the optimal operator-unit mapping arrangement. In some embodiments, the operational load balancing computing entity 106 generates the priority score for a work unit profile based on a work unit reward measure for the work unit profile, where the work unit reward measure for a work unit profile may be determined based on (e.g., by adding) each per-designation reward measure that is associated with a respective operational condition designation and the work unit profile. In some of the noted embodiments, each per-designation reward measure for a respective operational condition designation may be determined based on (e.g., by multiplying): (i) the unit-designation effectiveness measure for the respective operational condition designation and the work unit profile as determined by the unit-designation model; and (ii) the operational condition reward measure for the respective operational condition as determined based on the operational condition reward model.

At step/operation 407, the operational load balancing computing entity 106 performs one or more operational load balancing operations based on the optimal operator-unit mapping arrangement. In some embodiments, the operational load balancing computing entity 106 causes client computing devices to generate notifications for each operator profile that describes an assigned subset of the work unit profiles that is assigned to the operator profile by the optimal operator-unit mapping arrangement. In some embodiments, the operational load balancing computing entity 106 causes each operator profile to perform (e.g., in a priority order determined based on the priority scores determined at step/operation 406) an assigned subset of the work unit profiles that is assigned to the operator profile by the optimal operator-unit mapping arrangement.

In some embodiments, performing the one or more operational load balancing operations comprises, for each operator profile of the plurality of operator profiles, causing presentation of an operator queue user interface that describes an assigned subset of the plurality of work unit profiles that have been mapped to the operator profile according to the optimal operator-unit mapping arrangement. In some embodiments, the operator queue user interface presented to an operator profile of the plurality of operator profiles describes a priority score for each work unit profile in the assigned subset.

An operational example of an operator queue user interface 1100 configured to be presented to an operator end-user that is associated with an operator profile is depicted in FIG. 11. As depicted in FIG. 11, the operator queue user interface 1100 depicts a user interface region 1101 that depicts the completion rate of required claim processing actions with respect to five priority-score-based categories of work unit profiles. As further depicted in FIG. 11, the operator queue user interface 1100 depicts a user interface region 1102 that describes, for each work unit item assigned to the operator profile, various data fields including a priority category designation 1111.

In some embodiments, performing the one or more operational load balancing operations comprises causing presentation of an operational load balancing administration user interface on an administrator computing entity associated with an administrator user profile of the operational system. The operational system administration user interface may describe assignment of work unit profiles to operator profiles and/or priority scores for the assigned work unit profiles.

An operational example of an operational load balancing administration user interface 1200 is presented in FIG. 12. As depicted in FIG. 12, the operational load balancing administration user interface 1200 includes user interface region 1201 that describes, for each operator profile associated with the operational system, a work unit completion ratio of the operator profile. As further depicted in FIG. 12, the operational load balancing administration user interface 1200 depicts user interface region 1202 that describes overall work unit completion performance of all of the operator profiles associated with the operational system over time.

VI. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
   determining, by one or more processors, a plurality of constraint-satisfying operator-unit mapping arrangements that satisfy an operator unity constraint and an operator capacity constraint, wherein: (i) in accordance with the operator unity constraint, a constraint-satisfying operator-unit mapping arrangement of the plurality of constraint-satisfying operator-unit mapping arrangements maps a work unit profile of a plurality of work unit profiles to an operator profile of a plurality of operator profiles, and (ii) in accordance with the operator capacity constraint, a total operator utilization measure for the operator profile under a constraint-satisfying operator-unit mapping arrangement of the plurality of constraint-satisfying operator-unit mapping arrangements satisfies an estimated capacity of the operator profile;
   for the constraint-satisfying operator-unit mapping arrangement, determining, by the one or more processors and using an optimization-based ensemble machine learning model, an arrangement utility measure that describes an estimated utility of utilizing a mapping between the operator profile and the work unit profile;
   determining, by the one or more processors, an optimal operator-unit mapping arrangement based at least in part on the arrangement utility measure; and
   initiating, by the one or more processors, the performance of one or more operational load balancing operations based at least in part on the optimal operator-unit mapping arrangement.

2. The computer-implemented method of claim 1, wherein the arrangement utility measure is determined based at least in part on at least one of: (i) an operator-designation model that describes relationships between the plurality of operator profiles and one or more operational condition designations, (ii) a unit-designation model that describes relationships between each of the plurality of work unit profiles and the one or more operational condition designations, (iii) an operational condition reward model that describes an estimated reward of an operational condition designation of the one or more operational condition designations, or (iv) an operator cost-capacity model that describes an estimated cost and the estimated capacity for the operator profile.

3. The computer-implemented method of claim 2, wherein:
   the operator-designation model describes an operator-designation effectiveness measure for an operator-designation pair of a plurality of operator-designation pairs that comprises the operator profile and an operational condition designation of the one or more operational condition designations, and
   the operator-designation effectiveness measure for the operator-designation pair describes an estimated effectiveness of utilizing the operator profile for the operational condition designation that is associated with the operator-designation pair.

4. The computer-implemented method of claim 3, wherein:
   the unit-designation model describes a unit-designation effectiveness measure for a unit-designation pair of a plurality of unit-designation pairs that comprises the work unit profile and the operational condition designation, and
   the unit-designation effectiveness measure for the unit-designation pair describes an estimated effectiveness of utilizing the work unit profile for the operational condition designation.

5. The computer-implemented method of claim 3, wherein determining the arrangement utility measure for the constraint-satisfying operator-unit mapping arrangement comprises:
   determining an arrangement reward measure for the constraint-satisfying operator-unit mapping arrangement based at least in part on the unit-designation model, the operator-designation model, and the operational condition reward model for the work unit profile;
   determining an arrangement cost measure for the constraint-satisfying operator-unit mapping arrangement based at least in part on an operator cost model for the operator profile; and
   determining the arrangement utility measure based at least in part on the arrangement reward measure and the arrangement cost measure.

6. The computer-implemented method of claim 3, wherein:
   the optimization-based ensemble machine learning model is a stochastic optimization model, and
   the arrangement utility measure for the constraint-satisfying operator-unit mapping arrangement describes a stochastic arrangement utility measure for the constraint-satisfying operator-unit mapping arrangement.

7. The computer-implemented method of claim 6, wherein the stochastic arrangement utility measure for the constraint-satisfying operator-unit mapping arrangement is determined based at least in part on at least one of:
   an operator-designation probability distribution for the operator-designation pair,
   a unit-designation probability distribution for the unit-designation pair,
   an operational condition reward distribution for the work unit profile,
   an operator cost probability distribution for the operator profile, and
   an operator capacity probability distribution for the operator profile.

8. The computer-implemented method of claim 1, wherein performing the one or more operational load balancing operations comprises causing presentation of an operator queue user interface that is configured to display an assigned subset of the plurality of work unit profiles that have been mapped to the operator profile according to the optimal operator-unit mapping arrangement.

9. The computer-implemented method of claim 8, wherein the operator queue user interface is configured to display a priority score for each work unit profile in the assigned subset.

10. The computer-implemented method of claim 9, wherein the priority score for the work unit profile in the assigned subset is determined based at least in part on at least one of a work unit reward measure for the work unit profile.

11. The computer-implemented method of claim 1, wherein:
the plurality of work unit profiles describes a plurality of patient profiles,
the plurality of operator profiles describes a plurality of provider profiles, and
the one or more operational condition designations describe one or more medical condition profiles.

12. The computer-implemented method of claim 1, wherein:
the plurality of work unit profiles describes a plurality of medical record profiles,
the plurality of operator profiles describes a plurality of provider profiles, and
the one or more operational condition designations describe one or more medical condition profiles.

13. An apparatus comprising one or more processors and memory including program code, the memory and the program code configured to, with the one or more processors, cause the apparatus to at least:
determine a plurality of constraint-satisfying operator-unit mapping arrangements that satisfy an operator unity constraint and an operator capacity constraint, wherein: (i) in accordance with the operator unity constraint, a constraint-satisfying operator-unit mapping arrangement of the plurality of constraint-satisfying operator-unit mapping arrangements maps a work unit profile of a plurality of work unit profiles to an operator profile of a plurality of operator profiles, and (ii) in accordance with the operator capacity constraint, a total operator utilization measure for the operator profile under a constraint-satisfying operator-unit mapping arrangement of the plurality of constraint-satisfying operator-unit mapping arrangements satisfies an estimated capacity of the operator profile;
for the constraint-satisfying operator-unit mapping arrangement, determine, using an optimization-based ensemble machine learning model, an arrangement utility measure that describes an estimated utility of utilizing a mapping between the operator profile and the work unit profile;
determine an optimal operator-unit mapping arrangement based at least in part on the arrangement utility measure; and
initiate the performance of one or more operational load balancing operations based at least in part on the optimal operator-unit mapping arrangement.

14. The apparatus of claim 13, wherein the arrangement utility measure is determined based at least in part on at least one of: (i) an operator-designation model that describes relationships between the plurality of operator profiles and one or more operational condition designations, (ii) a unit-designation model that describes relationships between each of the plurality of work unit profiles and the one or more operational condition designations, (iii) an operational condition reward model that describes an estimated reward of an operational condition designation of the one or more operational condition designations, or (iv) an operator cost-capacity model that describes an estimated cost and the estimated capacity for the operator profile.

15. The apparatus of claim 14, wherein:
the operator-designation model describes an operator-designation effectiveness measure for an operator-designation pair of a plurality of operator-designation pairs that comprises the operator profile and an operational condition designation of the one or more operational condition designations, and
the operator-designation effectiveness measure for the operator-designation pair describes an estimated effectiveness of utilizing the operator profile for the operational condition designation that is associated with the operator-designation pair.

16. The apparatus of claim 14, wherein:
the unit-designation model describes a unit-designation effectiveness measure for a unit-designation pair of a plurality of unit-designation pairs that comprises the work unit profile and the operational condition designation, and
the unit-designation effectiveness measure for the unit-designation pair describes an estimated effectiveness of utilizing the work unit profile for the operational condition designation that is associated with the operator-designation pair.

17. A computer program product comprising at least one non-transitory computer-readable storage medium having computer-readable program code portions stored therein, the computer-readable program code portions configured to:
determine a plurality of constraint-satisfying operator-unit mapping arrangements that satisfy an operator unity constraint and an operator capacity constraint, wherein: (i) in accordance with the operator unity constraint, a constraint-satisfying operator-unit mapping arrangement of the plurality of constraint-satisfying operator-unit mapping arrangements maps a work unit profile of a plurality of work unit profiles to an operator profile of a plurality of operator profiles, and (ii) in accordance with the operator capacity constraint, a total operator utilization measure for the operator profile under a constraint-satisfying operator-unit mapping arrangement of the plurality of constraint-satisfying operator-unit mapping arrangements satisfies an estimated capacity of the operator profile;
for the constraint-satisfying operator-unit mapping arrangement, determine, using an optimization-based ensemble machine learning model, an arrangement utility measure that describes an estimated utility of utilizing a mapping between the operator profile and the work unit profile;
determine an optimal operator-unit mapping arrangement based at least in part on the arrangement utility measure; and
initiate the performance of one or more operational load balancing operations based at least in part on the optimal operator-unit mapping arrangement.

18. The computer program product of claim 17, wherein the arrangement utility measure is determined based at least in part on at least one of: (i) an operator-designation model that describes relationships between the plurality of operator profiles and one or more operational condition designations, (ii) a unit-designation model that describes relationships between each of the plurality of work unit profiles and the one or more operational condition designations, (iii) an operational condition reward model that describes an estimated reward of an operational condition designation of the one or more operational condition designations, or (iv) an operator cost-capacity model that describes an estimated cost and the estimated capacity for the operator profile.

19. The computer program product of claim 18, wherein:
the operator-designation model describes an operator-designation effectiveness measure for an operator-designation pair of a plurality of operator-designation pairs that comprises the operator profile and an operational condition designation of the one or more operational condition designations, and
the operator-designation effectiveness measure for the operator-designation pair describes an estimated effectiveness of utilizing the operator profile for the operational condition designation that is associated with the operator-designation pair.

20. The computer program product of claim 18, wherein:
the unit-designation model describes a unit-designation effectiveness measure for a unit-designation pair of a plurality of unit-designation pairs that comprises the work unit profile and the operational condition designation, and
the unit-designation effectiveness measure for the unit-designation pair describes an estimated effectiveness of utilizing the work unit profile for the operational condition designation that is associated with the operator-designation pair.

* * * * *